United States Patent [19]
Tanimoto et al.

[11] Patent Number: 5,891,663
[45] Date of Patent: Apr. 6, 1999

[54] PROCESS FOR PREPARING POLYPEPTIDE

[75] Inventors: Tadao Tanimoto; Masashi Kurimoto, both of Okayama, Japan

[73] Assignee: Kabushiki Kaisha Hayashibara Seibutsu Kagaku Kenkyujo, Okayama, Japan

[21] Appl. No.: 896,501

[22] Filed: Jul. 18, 1997

[30]     Foreign Application Priority Data

Jul. 25, 1996 [JP] Japan .................................. 8-213267
Jan. 31, 1997 [JP] Japan .................................. 9-031474

[51] Int. Cl.⁶ ............................ C12P 21/00; C07K 14/52
[52] U.S. Cl. ........................ 435/68.1; 530/351; 530/350; 530/412
[58] Field of Search .................................. 530/350, 412, 530/351; 435/68.1

[56]               References Cited

U.S. PATENT DOCUMENTS 4,276,282   6/1981   Sugimoto et al. .

FOREIGN PATENT DOCUMENTS 0 692 536    1/1995   European Pat. Off. .
0 712 931    5/1996   European Pat. Off. .
56-054158   12/1981   Japan .
08-027189    1/1996   Japan .
08-193098    7/1996   Japan .
08-231598    9/1996   Japan .

OTHER PUBLICATIONS

Thornberry, Nancy et al., "A novel hetewrodimeric cysteine protease is required for interleukin–1beta processing in monocytes.", Nature, vol. 356, pp. 768–774 (1992).

Miller, Douglas, et al., "Purification and characterization of active human interleukin–1beta converting enzyme from THP.1 monocytic cells.", J. Biological Chemistry, vol. 268, No. 24, pp. 18062–18069 (1993).

Kuroki, Toshio et al., Jikken–Igaku–Bessatsu–Saibo–Kogaku–Handbook, (1992).

Yokota, Takashi ed. et al., Jikken–Igaku–Bessatsu–Biomaterial Series 3, "Genetic Cloning Experimental Method" (1993).

Laemmli, U.K., "Cleavage of structural proteins during the assembly of the head of bacteriophage T4.", Nature, vol. 227, pp. 680–685 (1970).

Hay, Robert ed. et al., "Catalogue of cell lines & hybridomas.", 6th Ed. (1988).

Alnemri, Emad, et al., "Cloning and expression of four novel isoforms of human interleukin–1beta converting enzyme with different apoptotic activities.", J. Biol. Chemistry, vol. 270, No. 9, pp. 4312–4317 (1995).

*Primary Examiner*—Toni R. Scheiner
*Assistant Examiner*—Geetha P. Bansal
*Attorney, Agent, or Firm*—Browdy and Neimark

[57]                  ABSTRACT

A method for converting a precursor of a polypeptide that induces IFN-γ production in immunocompetent cells, characterized in that it comprises a step of contacting an interleukin-1β converting enzyme with the precursor to convert it into an active polypeptide that induces IFN-γ production in immunocompetent cells.

9 Claims, 2 Drawing Sheets

NOTE: IN THE FIGURE, THE SYMBOLS "●" AND "○" MEAN THE POLYPEPTIDE YIELDS WHEN INCUBATED AT 4°C AND 37°C, RESPECTIVELY.

PROCESS FOR PREPARING POLYPEPTIDE

BACKGROUND OF THE INVENTION

1. Field of the Invention

The present invention relates to a process for producing a physiologically active polypeptide, more particularly, to a process for producing a polypeptide that induces interferon-γ (hereinafter abbreviated as "IFN-γ") production in immunocompetent cells.

2. Description of the Prior Art

The present inventors succeeded in isolating a polypeptide that induces IFN-γ production in immunocompetent cells and a cDNA encoding the polypeptide, and disclosed them in Japanese Patent Kokai Nos.27,189/96 and 193,098/96. The polypeptide is featured in inducing the production of IFN-γ as a useful biologically active substance, enhancing the cytotoxicity by killer cells, and inducing the formation of killer cells; it can be expected for use as anti-virus agents, antiseptics, antitumor agents and anti-immunopathy agents.

It is said that, in human cells, polypeptides formed by the expression of genes may be processed by intracellular enzymes to be partially digested and to receive sugar chains. Polypeptides to be satisfactorily incorporated into pharmaceuticals may be those which were processed similarly as in human cells; such cells have a demerit that they less produce the present polypeptide as disclosed in Japanese Patent Application No.269,105/96. The present inventors' energetic study revealed that the present polypeptide usually exists in human cells in the form of a precursor with a molecular weight of about 24,000 daltons and no biological activity. Although it is not restricted to the present polypeptide, it is known that most cytokines are usually produced as precursors with no biological activity, and then processed by intracellular enzymes to be converted into active polypeptides.

SUMMARY OF THE INVENTION

The present inventors energetically studied to solve the object and found that an interleukin-1β converting enzyme (hereinafter abbreviated as "ICE") acts on a precursor of the polypeptide to convert it into an active polypeptide that induces IFN-γ production in immunocompetent cells.

The first object of the present invention is to provide an enzyme which acts on a precursor of a polypeptide that induces IFN-γ production in immunocompetent cells to convert the precursor into an active polypeptide which induces IFN-γ production in immunocompetent cells.

The second object of the present invention is to provide a method for producing the enzyme.

The third object of the present invention is to provide a method for converting the precursor into an active polypeptide that induces IFN-γ production in immunocompetent cells.

The present inventors energetically studied to solve the object and found that an enzyme, isolated from a human cell line, acts on a precursor of the polypeptide to convert it into an active polypeptide that induces IFN-γ production in immunocompetent cells. They confirmed that the enzyme can be produced from artificially proliferated cells, particularly, human hematopoietic cells, and accomplished this invention.

The first object of the present invention is solved by an enzyme which converts a precursor of a polypeptide which induces IFN-γ production in immunocompetent cells into an active polypeptide.

The second object of the present invention is solved by a process for producing the enzyme comprising culturing cells which produce the enzyme in nutrient culture media, and collecting the produced enzyme from the resultant cultures.

The third object of the present invention is solved by a conversion method for polypeptide comprising a step of contacting the enzyme with the precursor to convert it into an active polypeptide.

BRIEF DESCRIPTION OF THE ACCOMPANYING DRAWINGS

In the figures, "PCMV" means a cytomegalovirus promotor; "HuIGIF" means a CDNA encoding a precursor of the polypeptide according to the present invention; and "HuICE" means a cDNA encoding ICE.

DETAILED DESCRIPTION OF THE INVENTION

As reported by Nancy A. Thornberry et al. in "*Nature*", Vol.356, pp.768–774 (1992), ICE is a cysteine protease which has a heterodimer structure consisting of two subunits with respective molecular weights of about 20,000 and about 10,000 daltons, and usually expresses its activity in the form of coagulated heterodimers. ICE is in itself a conventional enzyme and known that it cleaves the peptide linkages between the aspartic acid 116 and alanine 117 and between the aspartic acid 27 and glycine 28 in the amino acid sequence of a precursor of interleukin-1β. However, it is not known that ICE acts on a precursor of a polypeptide, that incudes IFN-γ production in immunocompetent cells, to cleave the specific site, particularly, the peptide linkage between the aspartic acid 36 and tyrosine 37 in SEQ ID NO:1 to produce an active polypeptide that induces IFN-γ production in immunocompetent cells.

The present invention was made based on the finding of an enzyme which converts a precursor of a polypeptide that induces IFN-γ production in immunocompetent cells into an active polypeptide. The precursor as referred to in the present invention has a molecular weight of about 24,000 daltons on SDS-polyacrylamide gel electrophoresis (SDS-PAGE) in the presence of a reducing agent, and exists, for example, in cells capable of producing the polypeptide and mammalian host cells transformed by introducing a DNA, e.g., a DNA with the nucleotide sequence of SEQ ID NO:5 which contains a region encoding the polypeptide. Such a precursor contains a part of or the whole of the amino acid sequence of SEQ ID NO:1 at the N-terminal region, and in whole, contains the whole amino acid sequence of SEQ ID NO:2 (where the symbol "Xaa" is "isoleucine" or "threonine") and has a molecular weight of 18,000–19,500 daltons on SDS-PAGE in the presence of a reducing agent.

It is said that, in human cells, polypeptides formed by the expression of genes may be processed by intracellular enzymes to partially digest the polypeptides and add sugar chains thereunto. Polypeptides to be satisfactorily incorporated into pharmaceuticals may be those which received processings similarly as in human cells; such cells have a demerit that they less produce the present polypeptide as disclosed in Japanese Patent Application No.269,105/96. The present inventors' energetic study revealed that the polypeptide usually exists in human cells in the form of a precursor with a molecular weight of about 24,000 daltons and no biological activity. Although it is not restricted to the polypeptide, it is known that most cytokines are usually produced as precursors with no biological activity, and then processed by intracellular enzymes to be converted into active polypeptides.

The precursor as referred to in the present invention generally has a molecular weight of about 24,000 daltons on SDS-polyacrylamide gel electrophoresis (SDS-PAGE) in the presence of a reducing agent, and exists, for example, in cells which inherently produce the polypeptide and in mammalian host cells transformed by introducing a DNA, e.g., a DNA with the nucleotide sequence of SEQ ID NO:5, containing a region which encodes the polypeptide. Such a precursor contains a part of or the whole of the amino acid sequence of SEQ ID NO:1 at the N-terminal region, and in whole, contains either the whole amino acid sequence of SEQ ID NO:2 or one which partially lacks at least one amino acid at the N-terminal region and does not induce IFN-γ induction in immunocompetent cells.

However, when contacted with the precursor according to the present invention, ICE cleaves the polypeptide linkage between the aspartic acid 36 and tyrosine 37 in the amino acid sequence of SEQ ID NO:1 of the precursor to convert the precursor into an active polypeptide with the amino acid sequence of SEQ ID NO:3, causing the active polypeptide either with or without a cofactor to induce IFN-γ production in immunocompetent cells. The active polypeptide usually has the amino acid sequences of SEQ ID NO:3 at the N-terminal region and SEQ ID NO:4 as a whole, and a molecular weight of 18,000–19,500 daltons on SDS-PAGE in the presence of a reducing agent.

Any natural and artificially produced ICEs can be used in the present invention as long as they produce active polypeptides that induce IFN-γ production in immunocompetent cells independently of their structures, sources and origins. As reported by Emad S. Alnemri et al. in "The Journal of Biological Chemistry", Vol.270, No.9, pp.4,312–4,317 (1995), it is known that some ICEs even with the same origin may have some isoforms. These isomers are said to have slightly different physiological activities; they can be used in the present invention as long as they act on a precursor of the present polypeptide to form an active polypeptide.

Generally, ICE can be obtained from cells, which inherently produce it, and transformants obtained by applying recombinant DNA technology. Examples of such cells are those which were established from mammal and human cells such as epithelial cells, endothelial cells, interstitial cells, cartilage cells, monocytes, granulocytes, lymphocytes, and established cell lines thereof. Examples of the transformants include transformed microorganisms and animal cells obtained by introducing a DNA encoding ICE into microorganisms and animal cells. ICE is prepared by culturing these transformants in conventional culture media used in this field, either treating them with ultrasonics in the form of intact cultures or after separated from the cultures or soaking the transformants in hypotonic solvents, applying to the resulting cell debris or mixtures containing culture supernatants and cell debris the following conventional techniques used for purifying enzymes in this field; salting out, dialysis, filtration, concentration, separatory sedimentation, ion-exchange chromatography, gel filtration chromatography, adsorption chromatography, isoelectric chromatography, hydrophobic chromatography, reverse-phase chromatography, affinity chromatography, gel electrophoresis and electrofocusing. Two or more of these purification methods can be used in combination. The DNA encoding ICE and transformants which produce ICE are disclosed, for example, by Nancy A. Thornberry et al. in "Nature", Vol.356, pp.768–774 (1992) and by Emad S. Alnemri et al. in "The Journal of Biological Chemistry", Vol.270, No.9, pp.4,312–4,317 (1995).

Preferred embodiments to contact ICE with a precursor of the present polypeptide are effected, for example, by contacting ICE prepared by the above method with a precursor of the polypeptide or introducing a DNA encoding ICE and a DNA encoding the polypeptide into appropriate mammalian host cells to express both DNAs. In the former, cells which produce the precursor inherently or those which were transformed to produce the precursor are cultured in nutrient culture media. ICE, obtained in the above method, is allowed to coexist in the resulting cultures or added to the resulting mixtures or cell debris after disrupting the proliferated cells separated or unseparated from the cultures. Usually, a sufficient amount of ICE to be coexisted or added is not more than the equimolar of the precursor, and the ICE is contacted with the precursor at temperatures and pHs, which allow the ICE to act on the precursor, usually, the ICE is allowed to react with the precursor until the desired amount of active polypeptide is formed from the material precursor at temperatures of about 4°–40° C. and pHs of about 6–9. Thus, reaction mixtures containing the active polypeptide can be obtained. For the later described cells such as THP-1 cells (ATCC TIB 202) and A-253 cells (ATCC HTB 41) which produce both ICE and a precursor of the polypeptide, ICE is not necessarily be added to the cells. Only required is to incubate cultures containing the cells or cell debris, obtained by disrupting the cells on demand, at temperatures and pHs which can allow the ICE to act on the precursor to form an active polypeptide similarly as in the former case. In this case, adequate amounts of reducing agents such as 2-mercaptoethanol, dithiothreitol and reduced glutathione are preferably used in the incubation to effectively promote the reaction.

In the latter, a DNA encoding ICE and a DNA encoding a precursor of the polypeptide are both introduced into an appropriate mammalian host cell to transform it. In this case, ICE, formed by the DNA expression, acts on a precursor of the polypeptide, formed by the DNA expression in the same transformant, to form an active polypeptide. Examples of such host cells are epidermal-, interstitial-, neuroblast-, hematopoietic-cell lines, which are derived from humans, monkeys, mice and hamsters and used conventionally as hosts, such as 3T3 cells including 3T3-Swiss albino cells (ATCC CCL 92), C1271 cells (ATCC CRL 1616), CHO cells including CHO-K1 cells (ATCC CCL 61), CV-1 cells (ATCC CCL 70), COS cells including COS-1 cells (ATCC CCL 1650), HeLa cells (ATCC CCL 2), MOP cells including MOP-8 cells (ATCC CRL 1709) and mutants thereof. Methods to introduce a DNA encoding ICE and a DNA encoding a precursor of the polypeptide into the host cells include conventional DEAE-dextran method, phosphoric acid-calcium method, electroporation, lipofection, microinjection, and virus-infection method using retrovirus, Adenovirus, herpesvirus and vaccinia virus. In this case, vectors such as pCD, pcDL-SRα, pKY4, pCDM8, pCEV4, pME18S and pSV2-gpt, including appropriate promotors, enhancers, replication origins, termination sites, splicing sequences, polyadenylation sequences and/or selection markers can be used. Clones, which were observed to produce an active polypeptide, were selected by applying the colony hybridization method or choosing the desired clone from transformants after culturing in nutrient culture media. Cultures containing the active polypeptide can be obtained by culturing the cloned transformant with conventional nutrient culture used in this field. As for cells which inherently produce a precursor of the polypeptide and other cells which were transformed to produce the polypeptide, they may produce the precursor along with decomposing enzymes, which decompose the polypeptide to inactivate it, such as CPP32 and Mch-3. In this case, the coexistence of substances, which inhibit these enzymes' activities, such as acetyl-L-aspartyl-L-glutamyl-L-valyl-L-aspart-1-al in culture media or cultures containing cells or cell debris can inhibit the decomposition of the active polypeptide and increase the polypeptide yield. Recombinant DNA technologies using mammalian host cells are disclosed in detail in "Jikken-Igaku-Bessatsu-Saibo-Kogaku-Handbook", edited by Toshio KUROKI, Masaru TANIGUCHI and Mitsuo OSHIMURA (1992) and in "Jikken-Igaku-Bessatsu-Biomaterial Series 3, Genetic Cloning Experimental Method", edited by Takashi YOKOTA and Kenichi ARAI, edited by Yodo Publisher, Tokyo, Japan (1993).

In the present invention, the activity of ICE was assayed and expressed by units for activity according to the method by Douglas K. Miller et al. in "The Journal of Biological Chemistry", Vol.268, No.24, pp.18,062–18,069 (1993); place in a container 395 $\mu$l of 25 mM Hepes buffer (pH 7.5) containing 10 w/v % sucrose, 2 mM dithiothreitol and 0.1 w/v % 3-[(3-cholamidopropyl)dimethylammonio]-1-propanesulfonic acid (hereinafter abbreviated as "CHAPS"), add to the buffer 100 $\mu$l of a testing ICE solution and 5 $\mu$l of 10 mM dimethyl sulfoxide solution of N-(N-acetyl-tyrosyl)-valinyl-alanyl-aspartic acid-7-amino-4-methylcoumarinamide, and incubate the mixture at 30° C. for one hour. During the reaction, monitor the content of 7-amino-4-methylcoumarin, which was released as the reaction proceeded, by monitoring with a fluorometry the intensity of a fluorescent at a wavelength of 460 nm emitted by the excitation of a light with a wavelength of 380 nm. One unit activity of the enzyme is defined as the amount which releases one pmole of 7-amino-4-methylcoumarin per min under these reaction conditions.

The resulting reaction mixtures and cultures containing an active polypeptide can be used intact as an IFN-$\gamma$ inducer, and usually, cells in the cultures are disrupted by ultrasonics, cell lysis enzymes and/or surfactants, followed by separating the polypeptide from the resulting cells and cell debris by filtration, centrifugation, etc., and purifying the separated polypeptide. In the purification, the cultures free of cells or cell debris were purified by conventional purification methods used to purify biologically active substances in this field, for example, salting out, dialysis, filtration, concentration, separatory sedimentation, ion-exchange chromatography, gel filtration chromatography, adsorption chromatography, isoelectric chromatography, hydrophobic chromatography, reverse-phase chromatography, affinity chromatography, gel electrophoresis and electrofocusing. If necessary, two or more of these purification methods can be used in combination. The resulting purified polypeptide can be concentrated and lyophilized into a liquid or solid product to meet their final uses. The monoclonal antibody, as disclosed in Japanese Patent Kokai No.231,598/96 by the same applicant of the present invention, can be advantageously used to purify the polypeptide: For example, affinity chromatography using the monoclonal antibody can yield the desired polypeptide with a relatively-high purity in the lowest cost and labor.

As described above, the active polypeptide, obtained by the present method has an activity of inducing the production of IFN-$\gamma$ as a useful biologically active substance, enhances the killer cells' cytotoxicities and induces the killer cells' production. Thus, the polypeptide exerts a strong activity in the treatment and/or the prevention of IFN-$\gamma$ and/or killer cell-susceptive diseases. Since the active polypeptide obtained by the present method has a strong IFN-$\gamma$ inducibility, it generally induces a prescribed amount of IFN-$\gamma$ production with only a relatively-small amount. The active polypeptide does not substantially induce serious side effects even when administered to the body in a relatively-high dose because of its extremely-low toxicity, and has a merit that it smoothly induces a desired amount of IFN-$\gamma$ production without strictly controlling the dose in actual use. Japanese Patent Application No.28,722/96 by the same applicant of the present invention discloses in detail the uses of the active polypeptide as an agent for susceptive diseases.

The following examples explain the present invention:

EXAMPLE 1

Preparation of precursor

In 0.5-ml of a reaction tube were placed 10 $\mu$l of 10× PCR buffer, 8 $\mu$l of 2.5 mM dNTP, 0.5 $\mu$l of a 5 units/$\mu$l Taq DNA polymerase solution, and one ng of the recombinant DNA pHIGIF disclosed in Japanese Patent Kokai No.193,098/96 by the same applicant of the present invention. To the mixture were added oligonucleotides with nucleotide sequences of 5'-AAGGCCAGTGTGCTGGGCCTGGACA-GTCAGCAAGG-3' (SEQ ID NO:6) and 5'-ACAGCCAGTGTGATGGC TAGTCTTCGTTTTGAACAG-3' (SEQ ID NO:7), which were chemically synthesized based on the nucleotide sequence of SEQ ID NO:5 for a cDNA encoding a precursor of the polypeptide, in an amount of 20 pmole each, and volumed up to 100 $\mu$l with sterilized distilled water. The resulting mixture was in a conventional manner incubated 30 cycles in a sequential manner at 94° C. for one min, at 60 min for one min and at 72° C. for one min to effect PCR reaction. "TAKARA PCR AMPLIFICATION KIT" commercialized by Takara Shuzo Co., Ltd., Otsu, Shiga, Japan, was used as a reagent for the PCR reaction.

Figure 1:
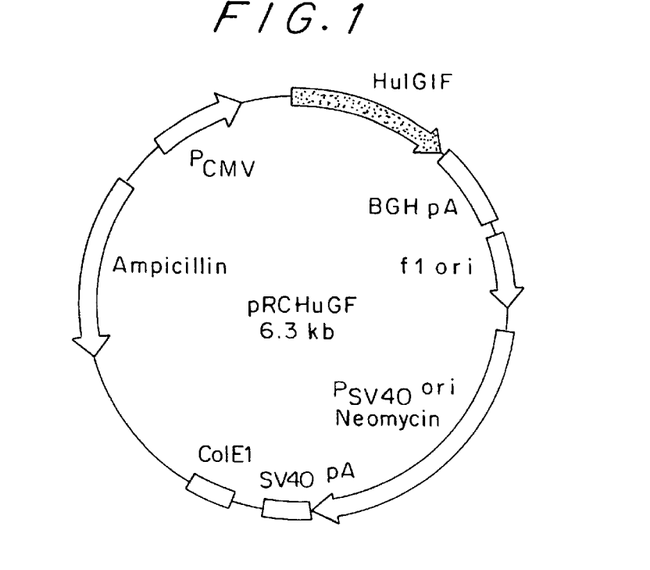
FIG. 1 is a structure of the recombinant DNA pRCHuGF containing a cDNA which encodes a precursor of the polypeptide according to the present invention.

The reaction product was in a conventional manner cleaved with a restriction enzyme, Bst XI, and 0.1 $\mu$g of the resulting DNA fragment with about 800 base pairs (bp) was placed in a container, dissolved in an adequate amount of sterilized distilled water, mixed with 10 ng of "pRc/CMV", a plasmid vector commercialized by Invitrogen BV, NV Leek, Netherlands, which had been cleaved with a restriction enzyme, Bst XI, and adequate amounts of 10× ligation buffer and T4 ligase, mixed with 10 mM ATP up to give a final concentration of one mM, followed by incubating the mixture at 16° C. for 18 hours to introduce the DNA fragment into the plasmid vector pRC/CMV. The recombinant DNA thus obtained was introduced into an *Escherichia coli* JM109 strain to obtain a transformant which was then inoculated to L-broth (pH 7.2) containing 50 $\mu$g/ml of ampicillin and incubated at 37° C. for 18 hours. Thereafter, the proliferated cells were collected from the culture and treated with the alkali-SDS method to extract a recombinant DNA. The recombinant DNA was named "pRCHuGF" and analyzed for nucleotide sequence using the Dideoxy method, revealing that it had the structure of FIG. 1. As shown in FIG. 1, the recombinant DNA pRCHuGF had cDNA HuIGIF, which consists of about 800 bp and encodes a precursor of the polypeptide, ligated to the downstream of a cytomegalovirus promotor, PCMV.

A seed culture of CHO-K1 cells (ATCC CCL 61) from chinese hamster's ovary was inoculated into Ham's F12 medium (pH 7.2) supplemented with 10 v/v % fetal calf serum and incubated for proliferation. Thereafter, the proliferated cells were collected, washed with phosphate buffered saline (hereinafter abbreviated as "PBS") and suspended in PBS to give a cell density of $1 \times 10^7$ cells/ml. 0.8 ml of the suspension and 10 μg of the recombinant DNA pRCHuGF were placed in a cuvette which was then ice-chilled for 10 min, set to "GENE PULSER™", an apparatus of electroporation commercialized by Japan Bio-Rad Laboratories, Tokyo, Japan, and charged once with a discharged pulse, followed by promptly removing the cuvette and ice-chilling it for 10 min. Thereafter, the cell suspension was recovered from the cuvette, inoculated into Ham's F12 medium (pH 7.2) supplemented with 10 v/v % fetal calf serum, incubated in a 5 v/v % $CO_2$ incubator at 37° C. for 3 days, then admixed with G418 to give a final concentration of 400 μg/ml and incubated for 3 days under the same conditions as above. Forty-eight colonies were selected from about 100 colonies, and some of the selected ones were inoculated into a culture plate distributed with Ham's F12 medium (pH 7.2) supplemented with 10 v/v % fetal calf serum, and cultured for a week similarly as above. Thereafter, the cells in each well in the plate were lysed by adding to each well 10 mM Tris-HCl buffer (pH 8.5) containing 5.1 mM magnesium chloride, 0.5 w/v % sodium deoxycholate, one w/v % "NONIDET P-40", a surfactant, 10 μg/ml aprotinin and 0.1 w/v % SDS.

Fifty μl aliquots of the resulting cell-lysate were placed in containers, followed by adding 50 μl glycerol and dithiothreitol in an amount which gave a final concentration of 2 w/v % to the containers, and allowing to stand the containers at 37° C. for one hour. Thereafter, the polypeptide in the cell-lysate was separated by SDS-polyacrylamide gel electrophoresis, and the polypeptide separated in the gel was in a conventional manner transferred to a nitrocellulose membrane, soaked for one hour in a previously obtained culture supernatant of a hybridoma, H-1 strain, which produces a monoclonal antibody specific to the polypeptide as disclosed in Japanese Patent Kokai No.231,598/96 applied by the same applicant of the present invention, and washed with 20 mM Tris-HCl buffer (pH 7.5) containing 0.05 v/v % tween 20 to remove an excessive amount of the monoclonal antibody. The nitrocellulose membrane was soaked for one hour in PBS containing rabbit antimouse immunoglobulin antibody labelled with horseradish peroxidase, washed with 50 mM Tris-HCl buffer (pH 7.5) containing 0.05 v/v % tween 20, and colored by soaking in 50 mM Tris-HCl buffer (pH 7.5) containing 0.005 v/v % hydrogen peroxide and 0.3 mg/ml diamino benzidine. Based on the coloration degree, a transformant clone, which more produced a precursor of the polypeptide, was selected and named "RCHuGF".

The transformant RCHuGF was inoculated into square culture flasks, into which were distributed Ham's F12 medium (pH 7.2) supplemented with 400 μg/ml G418 and 10 v/v % fetal calf serum, and incubated in a 5 v/v % $CO_2$ incubator at 37° C. for one week while replacing the medium with a fresh one on demand. Thereafter, an adequate amount of "TRYPSIN-EDTA", a trypsin commercialized by GIBCO Laboratories, Div. of Life Technologies, Inc., NY, USA, to detach the cells adhered to the walls of the flasks, and the detached cells were washed with PBS, further washed with ice-chilled 20 mM Hepes buffer (pH 7.4) containing 10 mM potassium chloride, 1.5 mM magnesium chloride and 0.1 mM ethylenediamine-N,N,N',N'-tetraacetic acid disodium salt, and allowed to stand for 20 min in 3-time volumes of a fresh preparation of the same buffer. The cells were then disrupted in a conventional manner, centrifuged at 10,000×g for 30 min to obtain a supernatant containing a precursor of the polypeptide. The precursor gave a molecular weight of about 24,000 daltons on SDS-polyacrylamide gel electrophoresis and had the amino acid sequence of SEQ ID NO:1 at the N-terminal region.

EXAMPLE 2
Preparation of ICE

In 0.5-ml of a reaction tube were placed one μl of 10× PCR buffer, 4 μl of 25 mM magnesium chloride, one μl of 10 mM dATP, one μl of 10 mM dGTP, one μl of 10 mM dCTP, one μl of 10 mM dTTP, one μl of 50 μM random hexanucleotide, one μl of 20 units/μl ribonuclease, one μl of 50 units/μl reverse transcriptase, one μg of a total RNA extract prepared in a conventional manner from THP-1 cells (ATCC TIB 202), a mononuclear cell line from a human acute monocytic leukemia, and the solution was volumed up with sterilized distilled water to give a total volume of 20 μl. The mixture solution was incubated at 42° C. for 30 min to effect reverse transcription reaction, followed by the incubation at 99° C. for 5 min to suspend the reaction.

To the reaction mixture were added 8 μl of 10× PCR buffer, 4 μl of 25 mM magnesium chloride, 0.5 μl of 5 units/μl of Taq DNA polymerase, and 20 pmole of oligonucleotides with nucleotide sequences of 5'-CTGCTCGAGACCATGGCCGACAAGGTCCTG-3' SEQ ID NO:8) and 5'-GAGGCGGCCGCTTAATGTCCTGGGAAGAG-3' SEQ ID NO:9), as a sense primer and an antisense primer, respectively, chemically synthesized based on a nucleotide sequence encoding a human ICE, and the solution was volumed up with a sterilized distilled water to give a total volume of 100 μl. The mixture was incubated 40 cycles in a sequential manner at 94° C. for one min, at 55° C. for one min, and at 72° C. for one min to effect PCR reaction. "GENE AMP RNA PCR KIT", a product of Perkin-Elmer Corp., Instrument Div., Norwalk, USA, was used as reagents for reverse transcription reaction and PCR reaction.

Figure 2:
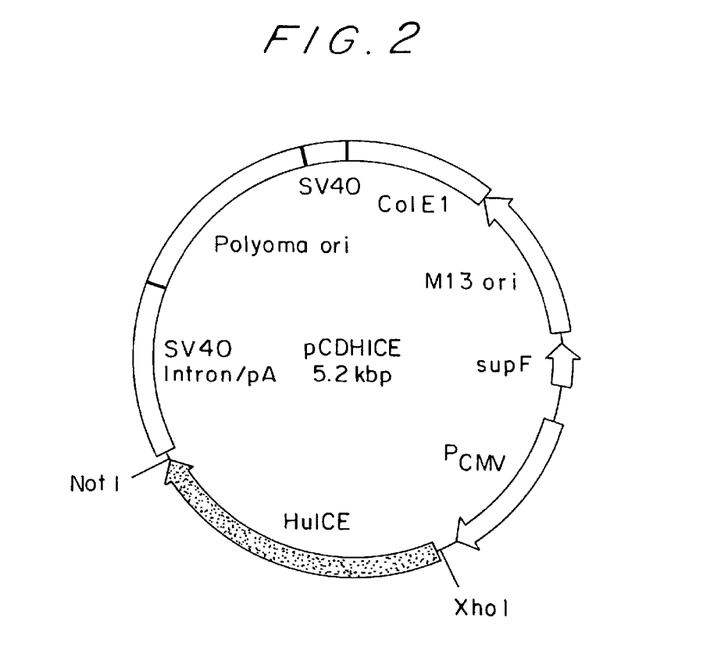
FIG. 2 is a structure of the recombinant DNA pCDHICE containing a cDNA which encodes ICE.

The reaction mixture thus obtained was in a conventional manner cleaved with restriction enzymes, Xho I and Not I, and the resulting DNA fragment of about 1,200 bp, which contained a region encoding the human ICE, was mixed with 10 ng of pCDM8, a plasmid vector commercialized by Invitrogen BV, NV Leek, Netherlands, which had been cleaved with the restriction enzymes Xho I and Not I, and adequate amounts of 10× ligation buffer and T4 DNA ligase, and further admixed with 10 mM ATP to give a final concentration of one mM, followed by the incubation at 16° C. for 18 hours to insert the above DNA fragment into the plasmid vector pCDM8. The recombinant DNA thus obtained was introduced into an *Escherichia coli* MC1061/P3 strain (ATCC 47035) by competent cell method to obtain a transformant which was then inoculated into L-broth (pH 7.2) containing 20 μg/ml ampicillin and 10 μg/ml tetracycline and incubated at 37° C. for 18 hours. The proliferated cells were collected from the resulting culture and treated with the alkali-SDS method to obtain a recombinant DNA pCDHICE which was then analyzed on dideoxy method, revealing that cDNA HuICE, which consists of about 1,200 bp containing a region encoding the human ICE, was ligated to the downstream of cytomegalovirus promotor PCMV as shown in FIG. 2.

According to a conventional method, a seed culture of COS-1 cells (ATCC CRL 1650), derived from African Green monkey kidney, was inoculated into and proliferated in DMEM medium (pH 7.4) supplemented with 10 v/v % fetal calf serum. The proliferated cells were collected from the culture, washed with a fresh preparation of the same medium and suspended in the medium to give a cell density of $2 \times 10^7$ cells/ml. 0.25 ml of the cell suspension and 10 µg of the above recombinant DNA pCDHICE were placed in a cuvette which was then incubated at ambient temperature for 10 min, set to "GENE PULSER™", an apparatus of electroporation commercialized by Japan Bio-Rad Laboratories, Tokyo, Japan, and charged once with a discharged pulse. Thereafter, the cuvette was removed from the apparatus and allowed to stand at ambient temperature for 10 min, followed by collecting the cells in the cuvette, inoculated into a petri dish with DMEM medium (pH 7.4) supplemented with 10 v/v % fetal calf serum, and incubated in a 5 v/v % $CO_2$ incubator at 37° C. for 2 days.

From the culture a supernatant was removed by sacking, and the resulting cells adhered to the bottom walls of the petri dish were washed with PBS, charged with an adequate amount of PBS containing 5 mM ethylenediamine-N,N,N',N'-tetraacetic acid disodium salt, and allowed to stand at ambient temperature for 10 min, followed by collecting cells detached from the petri dish. The cells thus obtained were washed with PBS, mixed with an adequate amount of 20 mM Hepes buffer (pH 7.4) containing 10 mM potassium chloride, 1.5 mM magnesium chloride, 0.1 mM ethylenediamine-N,N,N',N'-tetraacetic acid disodium salt, and one mM (4-amidino-phenyl)-methane-sufonylfluoride, and homogenized by a homogenizer under ice-chilling conditions. The disrupted cells were centrifuged at 1,500×g for 5 min to obtain a supernatant which was further centrifuged at 22,500×g for 60 min to obtain a supernatant containing 230 units/ml of ICE.

EXAMPLE 3
Preparation of polypeptide

A substrate solution was prepared by dissolving the precursor of the polypeptide in Example 1 in 100 mM Hepes buffer (pH 7.4), containing 10 v/v % glycerol, 0.1 w/v % CHAPS and 2 mM dithiothreitol, to give a concentration of 500 nM, and mixed with the ICE in Example 2 to give a concentration of 500 units/ml, followed by the incubation at 37° C. At 0 min, 10 min, 30 min, one hour, 3 hours, 6 hours and 18 hours after initiating the incubation, a portion of the reaction mixture was sampled at each sampling time and admixed with iodoacetamide to give a final concentration of 200 µg/ml to suspend the reaction. The Western Blotting method using the monoclonal antibody, as disclosed in Japanese Patent Kokai No.231,098/96 applied by the same applicant of the present invention, was applied to the reaction mixture to study the change on passage of time during the conversion of the precursor into an active polypeptide. The results were in FIG. 3.

The content of the active polypeptide in each sample, collected at each sampling time, was estimated by a bioassay using, as a competent cell, KG-1 cells (ATCC CCL 246), a mononuclear cell line from a human acute myelocytic leukemia. The bioassay was as follows: KG-1 cells were suspended in RPMI 1640 medium (pH 7.4) supplemented with 10 v/v % fetal calf serum to give a cell density of $1.5 \times 10^6$ cells/ml, and the cell suspension was distributed to a 96-well microplate in an amount of 0.1 ml/well. To the microplate was added the above reaction mixture after diluted with RPMI 1640 medium (pH 7.4) supplemented with 10 v/v % fetal calf serum in a volume of 0.1 ml/well, followed by incubating the microplate in a 5 v/v % $CO_2$ incubator at 37° C. for 24 hours. After completion of the incubation, 0.1 ml aliquots of the supernatants in the microplate's wells were sampled and quantified for IFN-γ using conventional enzyme immunoassay. A system free of the reaction mixture as a control was provided and treated similarly as above. The IFN-γ content in Table 1 was expressed after converted into international units with respect to an IFN-γ standard, Gg23-901-530, obtained from the National Institutes of Health (NIH), USA.

TABLE 1

| Reaction time (min) | IFN-γ content (IU/ml) |
| --- | --- |
| 0 min | 230 |
| 10 min | 520 |
| 30 min | 950 |
| 1 hour | 1,500 |
| 3 hours | 2,900 |
| 6 hours | 3,900 |
| 18 hours | 4,000 |

Figure 3:
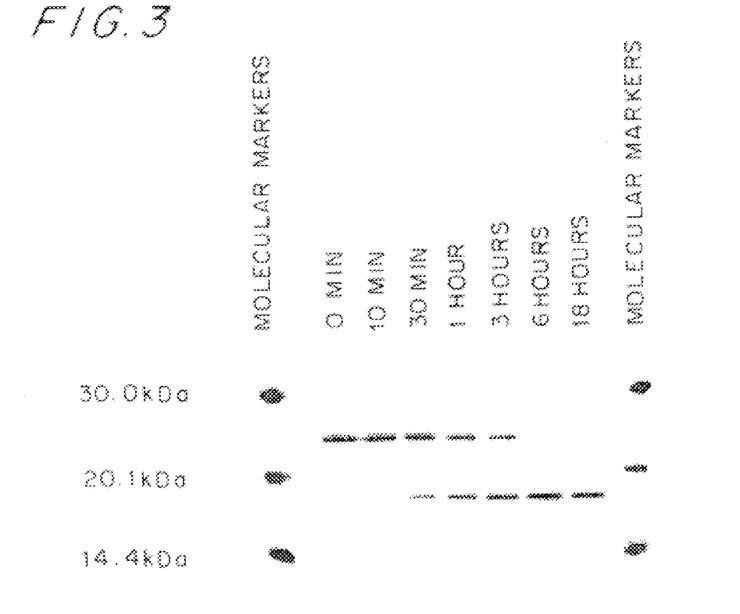
FIG. 3 is an intermediate picture, displayed on a screen and visualized by the Western Blotting, of a gel electrophoresis pattern which shows the change on passage of time during the conversion of a precursor of the present polypeptide into an active polypeptide.

As shown in the Western Blotting of Fig. 3, under this reaction conditions, a protein band with a molecular weight of about 24,000 daltons, corresponding to the precursor, gradually disappeared up to 3 hours after the initiation of the reaction, while a band with a molecular weight of about 18,200 daltons appeared. The IFN-γ content in Table 1 well agreed with the results; the producibility of IFN-γ as a reaction product gradually increased as a band with a molecular weight of about 18,200 daltons, corresponding to the active polypeptide. These results indicate that the ICE acted on a precursor of the polypeptide to form an active polypeptide that induces IFN-γ production in immunocompetent cells.

EXAMPLE 4
Physicochemical properties of active Polypeptide

EXAMPLE 4-1
Purification of polypeptide

The reaction mixture after an 18 hours' incubation in Example 3 was dialyzed against 10 mM phosphate buffer (pH 6.8), fed to a column of "DEAE 5PW", a gel for ion-exchange chromatography commercialized by Tosoh Corporation, Tokyo, Japan, which had been equilibrated with 10 mM phosphate buffer (pH 6.8), and fed with a linear gradient buffer of sodium chloride increasing from 0M to 0.5M in 10 mM phosphate buffer (pH 6.8), followed by collecting fractions eluted at sodium chloride concentrations of about 0.2–0.3M.

The fractions were pooled, dialyzed against PBS and fed to a column which had been prepared by providing a gel for immunoaffinity chromatography using a monoclonal antibody according to the method in Japanese Patent Kokai No.231,598/96 applied by the same applicant of the present invention, injecting the gel into a plastic cylindrical column, and washing the column with PBS. The column was fed with 100 mM glycine-HCl buffer (pH 2.5) to collect fractions containing an active polypeptide which induces IFN-γ production in immunocompetent cells. The fractions were pooled, dialyzed against sterilized distilled water, concentrated with a membrane filter, and lyophilized to obtain a purified polypeptide in a solid form. The theoretical yield was about 60% to the precursor used as the material.

EXAMPLE 4-2
Molecular weight of polypeptide

In accordance with the method as reported by U. K. Lemuli in "Nature", Vol.227, pp.680–685 (1970), the purified polypeptide in Example 4-1 was electrophoresed in a polyacrylamide gel in the presence of 2 w/v % dithiothreitol as a reducing agent to show a major band in a position corresponding to about 18,000–19,500 daltons. The data shows that ICE acted on a precursor of the polypeptide with a molecular weight of about 24,000 daltons to convert it into an active polypeptide with a molecular weight lower than that of the precursor. The molecular markers used in this experiment were calf serum albumin with a molecular weight of 67,000 daltons, ovalbumin with a molecular weight of 45,000, carbonic acid anhydrase with a molecular weight of 30,000 daltons, soy bean trypsin inhibitor with a molecular weight of 20,100 daltons, and α-lactalbumin with a molecular weight of 14,400 daltons.

EXAMPLE 4-3
Amino acid sequence of polypeptide at the N-terminal region

A conventional analysis using "MODEL 473A", a protein sequencer commercialized by Applied Biosystems, Inc., Foster City, USA, revealed that the purified polypeptide in Example 4-1 had the amino acid sequences of SEQ ID NO:3 at the N-terminal region. The data indicates that ICE acted on a precursor of the polypeptide to cleave the polypeptide linkage between the aspartic acid 36 and tyrosine 37.

EXAMPLE 5
Preparation of polypeptide

According to a conventional method, a seed culture of COS-1 cells (ATCC CRL 1650), derived from African Green monkey kidney, was inoculated into and proliferated in DMEM medium (pH 7.4) supplemented with 10 v/v % fetal calf serum. The proliferated cells were collected from the culture, washed with a fresh preparation of the same medium and suspended in the medium to give a cell density of $2 \times 10^7$ cells/ml. 0.25 ml of the cell suspension, 10 μg of the recombinant DNA pRCHuGF in Example 1, and 10 μg of the recombinant DNA pCDHICE in Example 2 were placed in a cuvette which was then incubated at ambient temperature for 10 min, set to "GENE PULSER™", an apparatus of electroporation commercialized by Japan Bio-Rad Laboratories, Tokyo, Japan, and charged once with a discharged pulse. The cuvette was then removed from the apparatus and allowed to stand at ambient temperature for 10 min, followed by collecting the cells in the cuvette, inoculated into a petri dish with DMEM medium (pH 7.4) supplemented with 10 v/v % fetal calf serum, and incubated in a 5 v/v % $CO_2$ incubator at 37° C. for 3 days.

From the culture a supernatant was removed by sacking, and the cells adhered to the bottom walls of the petri dish were washed with PBS, charged with an adequate amount of PBS containing 5 mM ethylenediamine-N,N,N',N'-tetraacetic acid disodium salt, and allowed to stand at ambient temperature for 10 min, followed by collecting cells detached from the petri dish. The cells thus obtained were washed with PBS, mixed with an adequate amount of 20 mM Hepes buffer (pH 7.4) containing 10 mM potassium chloride, 1.5 mM magnesium chloride, and 0.1 mM ethylenediamine-N,N,N',N'-tetraacetic acid disodium salt, and homogenized by a homogenizer under ice-chilling conditions. The disrupted cells were centrifuged at 1,000×g for 5 min to obtain a supernatant, followed by quantifying the polypeptide in the supernatant by applying an enzyme immunoassay using a monoclonal antibody specific to the polypeptide.

In parallel, a system free of the recombinant DNA pRCHuGF and/or the recombinant DNA PCDHICE was provided and treated similarly as above. The results were in Table 2.

TABLE 2

| Recombinant DNA | Yield of polypeptide (ng per $10^7$ cells) | Note |
|---|---|---|
| pRCHuGF + pCDHICE | 1,281.4 | Present invention |
| pRCHuGF | 25.8 | Control |
| PCDHICE | 15.1 | Control |
| No use | 0.1 | Control |

The results in Table 2 show that a DNA encoding a precursor of the polypeptide and a DNA encoding ICE satisfactorily express their expression products in COS-1 cells (ATCC CRL 1650), that the produced ICE effectively acted on the produced precursor to form an active polypeptide that induces IFN-γ production in immunocompetent cells. As shown in Table 2, such an active polypeptide was formed with only a slight amount in the control systems free of the above DNA(s). This fact evidences that the above DNAs satisfactorily expressed their expression products in COS-1 cells (ATCC CRL 1650).

The resulting active polypeptide was purified by applying the purification methods in Example 4-1 to the culture supernatant of COS-1 cells (ATCC CRL 1650) introduced with the above DNAs, and the purified polypeptide was determined for molecular weight by applying the method in Example 4-2 to reveal a main band, corresponding to a molecular weight of about 18,000–19,500 daltons, for polypeptide that induces IFN-γ production. Further application of the method in Example 4-3 has shown that the purified polypeptide has an amino acid sequence of SEQ ID NO:3 at the N-terminal region.

EXAMPLE 6
Preparation of polypeptide

New born hamsters were in a conventional manner injected with a rabbit antithymus serum to reduce their immunoreaction, transplanted with about $1 \times 10^4$ cells/head of A-253 cells (ATCC HTB 41), an epidermoid carcinoma, submaxillary gland, human, to their dorsal subcutaneous tissues, and fed for 32 days in an usual manner. Tumor masses formed subcutaneously, about 5 g weight per hamster, were extracted, cut, washed with 20 mM Hepes buffer (pH 7.4) containing 10 mM potassium chloride, 1.5 mM magnesium chloride, and 0.1 mM ethylenediamine-N,N,N',N'-tetraacetic acid disodium salt, and freezed at −20° C.

The freezed tumor small masses were thawed, admixed with one ml of a fresh preparation of the same hypotonic solution containing 10 mM 2-mercaptoethanol against one g of the wet tumor masses, treated with polythoron to disrupt cells, and centrifuged at 2,500 rpm for 10 min to obtain a supernatant containing about 500 units/ml of ICE. While incubating at 4° C. or 37° C., the supernatant was sampled at prescribed time intervals, followed by quantifying an active polypeptide by applying an enzyme immunoassay using a monoclonal antibody specific to the polypeptide. The results were in FIG. 4.

Figure 4:
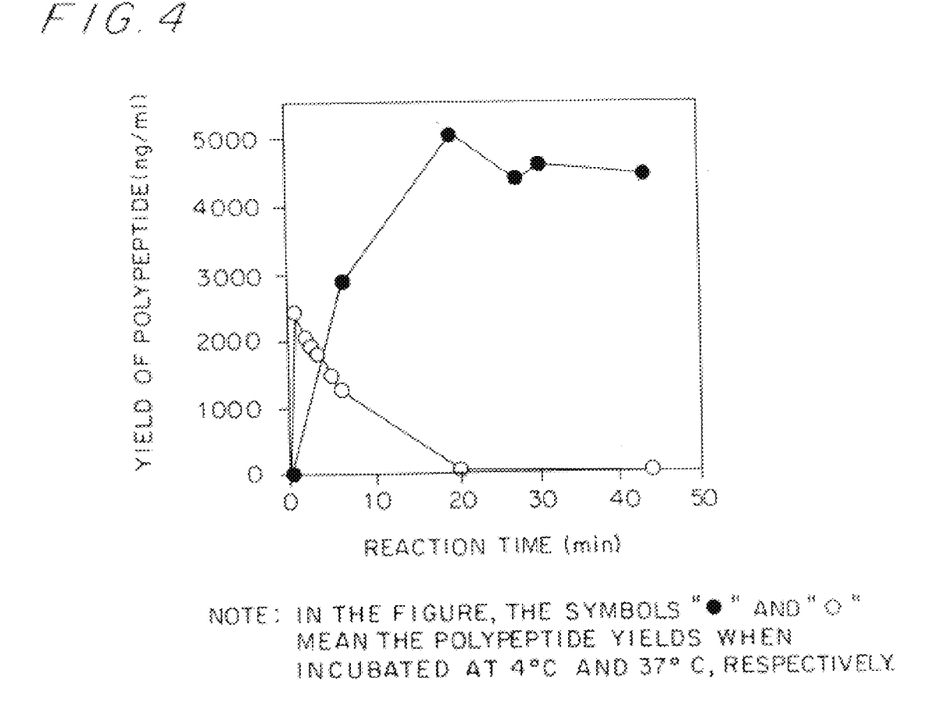
FIG. 4 is a figure which shows the formation dynamics of the polypeptide according to the present invention when the A-253 cells' extract was incubated at different temperatures.

As shown in FIG. 4, the incubation of the A-253 cells' extract effectively increases the polypeptide yield, and this means that, in the extract containing ICE and a precursor of the polypeptide, the ICE effectively acted on the precursor to form an active polypeptide. Lower temperatures are preferable as the incubation temperature, and the polypeptide yield with an incubation temperature of 4° C. was significantly higher than that with an incubation temperature of 37° C., e.g., the incubations at temperatures of 4° C. and 37° C. yielded 5.0 μg and 2.5 μg of the polypeptide per one g of wet tumor mass, respectively.

The reaction mixture containing the active polypeptide thus obtained was purified by the method in Example 4-1 and lyophilized, then determined for molecular weight by applying the method in Example 4-2 to observe a main band, corresponding to a molecular weight of about 18,000–19,500 daltons, for a polypeptide that induces IFN-γ production. The application of the method in Example 4-3 showed that the purified polypeptide had the amino acid sequence of SEQ ID NO:3 at the N-terminal region. Using dithiothreitol or reduced glutathione in place of the 2-mercaptoethanol used in the above, the tumor masses were treated similarly as above, revealing that all the reducing agents including 2-mercaptoethanol strongly increased the polypeptide yield at a concentration of one mM.

As described above, the present invention was made based on the original finding that ICE acts on a precursor of a polypeptide, that induces IFN-γ production in immuno-competent cells, to form an active polypeptide. The present invention uses such an activity of ICE and enables the production of a polypeptide as a useful pharmaceutical, which received similar processings as in human cells, is obtained by (i) contacting ICE with either cells which inherently produce the polypeptide or a precursor of the polypeptide produced from mammalian host cells which had been transformed by introducing a DNA containing a region encoding the polypeptide, or (ii) introducing both a DNA encoding ICE and a DNA containing a region encoding the polypeptide into mammalian host cells to express both the DNAs.

The present invention with these useful functions and activities would be a significant invention that strongly contributes to this field.

While there has been described what is at present considered to be the preferred embodiments of the invention, it will be understood the various modifications may be made therein, and it is intended to cover in the appended claims all such modifications as fall within the true spirit and scope of the invention.

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear     ( i i ) MOLECULE TYPE: peptide     ( v ) FRAGMENT TYPE: N-terminal fragment     ( x i ) SEQUENCE DESCRIPTION: SEQ ID NO: 1:

```
Met  Ala  Ala  Glu  Pro  Val  Glu  Asp  Asn  Cys  Ile  Asn  Phe  Val  Ala  Met
 1                   5                        10                       15

Lys  Phe  Ile  Asp  Asn  Thr  Leu  Tyr  Phe  Ile  Ala  Glu  Asp  Asp  Glu  Asn
              20                        25                       30

Leu  Glu  Ser  Asp  Tyr  Phe  Gly  Lys  Leu
              35                        40
```

( 2 ) INFORMATION FOR SEQ ID NO: 2:

( i ) SEQUENCE CHARACTERISTICS:
        ( A ) LENGTH: 193 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO: 2:

```
Met  Ala  Ala  Glu  Pro  Val  Glu  Asp  Asn  Cys  Ile  Asn  Phe  Val  Ala  Met
-35                 -30                       -25

Lys  Phe  Ile  Asp  Asn  Thr  Leu  Tyr  Phe  Ile  Ala  Glu  Asp  Asp  Glu  Asn
-20                      -15                      -10                      -5

Leu  Glu  Ser  Asp  Tyr  Phe  Gly  Lys  Leu  Glu  Ser  Lys  Leu  Ser  Val  Ile
              1                         5                        10
```

Arg Asn Leu Asn Asp Gln Val Leu Phe Ile Asp Gln Gly Asn Arg Pro
            15                  20                      25

Leu Phe Glu Asp Met Thr Asp Ser Asp Cys Arg Asp Asn Ala Pro Arg
        30                  35                  40

Thr Ile Phe Ile Ile Ser Met Tyr Lys Asp Ser Gln Pro Arg Gly Met
45                      50                  55                  60

Ala Val Thr Ile Ser Val Lys Cys Glu Lys Ile Ser Xaa Leu Ser Cys
                65                      70                  75

Glu Asn Lys Ile Ile Ser Phe Lys Glu Met Asn Pro Pro Asp Asn Ile
            80                      85                  90

Lys Asp Thr Lys Ser Asp Ile Ile Phe Phe Gln Arg Ser Val Pro Gly
        95                      100                 105

His Asp Asn Lys Met Gln Phe Glu Ser Ser Ser Tyr Glu Gly Tyr Phe
    110                     115                 120

Leu Ala Cys Glu Lys Glu Arg Asp Leu Phe Lys Leu Ile Leu Lys Lys
125                     130                     135                 140

Glu Asp Glu Leu Gly Asp Arg Ser Ile Met Phe Thr Val Gln Asn Glu
                145                     150                 155

Asp ( 2 ) INFORMATION FOR SEQ ID NO: 3:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( v ) FRAGMENT TYPE: N-terminal fragment ( x i ) SEQUENCE DESCRIPTION: SEQ ID NO: 3:

Tyr Phe Gly Lys Leu
1               5

( 2 ) INFORMATION FOR SEQ ID NO: 4:

( i ) SEQUENCE CHARACTERISTICS:
( A ) LENGTH: 157 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 4:

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Xaa Leu Ser Cys Glu Asn Lys Ile
65                  70                  75                  80

Ile Ser Phe Lys Glu Met Asn Pro Pro Asp Asn Ile Lys Asp Thr Lys
            85                  90                  95

Ser Asp Ile Ile Phe Phe Gln Arg Ser Val Pro Gly His Asp Asn Lys

|     |     |     |     |     | 100 |     |     |     | 105 |     |     |     | 110 |     |
|-----|-----|-----|-----|-----|-----|-----|-----|-----|-----|-----|-----|-----|-----|-----|
| Met | Gln | Phe | Glu | Ser | Ser | Ser | Tyr | Glu | Gly | Tyr | Phe | Leu | Ala | Cys | Glu |
|     |     | 115 |     |     |     |     | 120 |     |     |     |     | 125 |     |     |

Lys Glu Arg Asp Leu Phe Lys Leu Ile Leu Lys Lys Glu Asp Glu Leu
    130             135                 140

Gly Asp Arg Ser Ile Met Phe Thr Val Gln Asn Glu Asp
145             150                 155

( 2 ) INFORMATION FOR SEQ ID NO: 5:

( i ) SEQUENCE CHARACTERISTICS:
        ( A ) LENGTH: 579 base pairs
        ( B ) TYPE: nucleic acid
        ( C ) STRANDEDNESS: single
        ( D ) TOPOLOGY: linear     ( i i ) MOLECULE TYPE: cDNA to mRNA     ( i x ) FEATURE:
        ( A ) NAME/KEY: leader peptide
        ( B ) LOCATION: 1..108
        ( C ) IDENTIFICATION METHOD: S
        ( A ) NAME/KEY: mat peptide
        ( B ) LOCATION: 109..579
        ( C ) IDENTIFICATION METHOD: S     ( x i ) SEQUENCE DESCRIPTION: SEQ ID NO: 5:

```
ATG  GCT  GCT  GAA  CCA  GTA  GAA  GAC  AAT  TGC  ATC  AAC  TTT  GTG  GCA  ATG      48
Met  Ala  Ala  Glu  Pro  Val  Glu  Asp  Asn  Cys  Ile  Asn  Phe  Val  Ala  Met
-35            -30                      -25

AAA  TTT  ATT  GAC  AAT  ACG  CTT  TAC  TTT  ATA  GCT  GAA  GAT  GAT  GAA  AAC      96
Lys  Phe  Ile  Asp  Asn  Thr  Leu  Tyr  Phe  Ile  Ala  Glu  Asp  Asp  Glu  Asn
-20            -15                      -10                            -5

CTG  GAA  TCA  GAT  TAC  TTT  GGC  AAG  CTT  GAA  TCT  AAA  TTA  TCA  GTC  ATA     144
Leu  Glu  Ser  Asp  Tyr  Phe  Gly  Lys  Leu  Glu  Ser  Lys  Leu  Ser  Val  Ile
               1              5                           10

AGA  AAT  TTG  AAT  GAC  CAA  GTT  CTC  TTC  ATT  GAC  CAA  GGA  AAT  CGG  CCT     192
Arg  Asn  Leu  Asn  Asp  Gln  Val  Leu  Phe  Ile  Asp  Gln  Gly  Asn  Arg  Pro
          15              20                          25

CTA  TTT  GAA  GAT  ATG  ACT  GAT  TCT  GAC  TGT  AGA  GAT  AAT  GCA  CCC  CGG     240
Leu  Phe  Glu  Asp  Met  Thr  Asp  Ser  Asp  Cys  Arg  Asp  Asn  Ala  Pro  Arg
     30                   35                          40

ACC  ATA  TTT  ATT  ATA  AGT  ATG  TAT  AAA  GAT  AGC  CAG  CCT  AGA  GGT  ATG     288
Thr  Ile  Phe  Ile  Ile  Ser  Met  Tyr  Lys  Asp  Ser  Gln  Pro  Arg  Gly  Met
45                  50                       55                             60

GCT  GTA  ACT  ATC  TCT  GTG  AAG  TGT  GAG  AAA  ATT  TCA  AYT  CTC  TCC  TGT     336
Ala  Val  Thr  Ile  Ser  Val  Lys  Cys  Glu  Lys  Ile  Ser  Xaa  Leu  Ser  Cys
               65                       70                        75

GAG  AAC  AAA  ATT  ATT  TCC  TTT  AAG  GAA  ATG  AAT  CCT  CCT  GAT  AAC  ATC     384
Glu  Asn  Lys  Ile  Ile  Ser  Phe  Lys  Glu  Met  Asn  Pro  Pro  Asp  Asn  Ile
               80                       85                        90

AAG  GAT  ACA  AAA  AGT  GAC  ATC  ATA  TTC  TTT  CAG  AGA  AGT  GTC  CCA  GGA     432
Lys  Asp  Thr  Lys  Ser  Asp  Ile  Ile  Phe  Phe  Gln  Arg  Ser  Val  Pro  Gly
          95                       100                     105

CAT  GAT  AAT  AAG  ATG  CAA  TTT  GAA  TCT  TCA  TCA  TAC  GAA  GGA  TAC  TTT     480
His  Asp  Asn  Lys  Met  Gln  Phe  Glu  Ser  Ser  Ser  Tyr  Glu  Gly  Tyr  Phe
     110                 115                          120

CTA  GCT  TGT  GAA  AAA  GAG  AGA  GAC  CTT  TTT  AAA  CTC  ATT  TTG  AAA  AAA     528
Leu  Ala  Cys  Glu  Lys  Glu  Arg  Asp  Leu  Phe  Lys  Leu  Ile  Leu  Lys  Lys
125                 130                      135                            140

GAG  GAT  GAA  TTG  GGG  GAT  AGA  TCT  ATA  ATG  TTC  ACT  GTT  CAA  AAC  GAA     576
Glu  Asp  Glu  Leu  Gly  Asp  Arg  Ser  Ile  Met  Phe  Thr  Val  Gln  Asn  Glu
                    145                      150                      155
```

```
G A C                                                                                                    5 7 9
A s p
```

( 2 ) INFORMATION FOR SEQ ID NO:6:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:6:

```
A A G G C C A G T G    T G C T G G G C C T    G G A C A G T C A G    C A A G G                          3 5
```

( 2 ) INFORMATION FOR SEQ ID NO:7:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:7:

```
A A G G C C A G T G    T G C T G G G C C T    G G A C A G T C A G    C A A G G                          3 5
```

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:8:

```
C T G C T C G A G A    C C A T G G C C G A    C A A G G T C C T G                                       3 0
```

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:9:

```
G A G G C G G C C G    C T T A A T G T C C    T G G G A A G A G                                         2 9
```

We claim:

1. A process for producing an active polypeptide that induces interferon-γ production in an immunocompetent cell, which comprises the steps of:

(i) contacting interleukin-1β-converting enzyme with a precursor polypeptide to convert said precursor polypeptide into an active polypeptide which induces interferon-γ production in an immunocompetent cell, said precursor polypeptide comprising an amino acid sequence of SEQ ID NO:1 or a portion thereof, which maintains the aspartic acid 36 and tyrosine 37 residues in the amino sequence of SEQ ID NO:1 as a cleavage site for said interleukin-1β-converting enzyme, as an N-terminal sequence, and an amino acid sequence corresponding to residues 6 to 157 of SEQ ID NO:4, where Xaa is isoleucine or threonine; and (ii) collecting the active polypeptide.

2. The process of claim 1, wherein said precursor comprises the amino acid sequence of SEQ ID NO:2 where Xaa, an amino acid, is isoleucine or threonine.

3. The process of claim 1, wherein said active polypeptide contains the amino acid sequence of SEQ ID NO:3 at the N-terminal region.

4. The process of claim 1, wherein said active polypeptide contains the amino acid sequence of SEQ ID NO:4 where Xaa, an amino acid, is isoleucine or threonine.

5. The process of claim 1, wherein said precursor is contacted with the equimolar or lower amount of said interleukin-1β converting enzyme at a temperature of 4°–40° C.

6. The process of claim 1, wherein said precursor is contacted with the equimolar or lower amount of said interleukin-1β converting enzyme at a pH of about 6–9.

7. The process of claim 1, wherein said interleukin-1β converting enzyme is allowed to act on said precursor in the presence of a reducing agent.

8. The process of claim 7, wherein said reducing agent is one or more members selected from the group consisting of 2-mercaptoethanol, dithiothreitol and reduced glutathione.

9. The process of claim 1, wherein said active polypeptide is purified by one or more techniques selected from the group consisting of salting out, dialysis, filtration, concentration, separatory sedimentation, ion-exchange chromatography, gel filtration chromatography, adsorption chromatography, isoelectric chromatography, hydrophobic chromatography, reverse-phase chromatography, affinity chromatography, gel electrophoresis and electrofocusing.

* * * * *